United States Patent [19]

Jaraczewski et al.

[11] Patent Number: 4,817,613
[45] Date of Patent: Apr. 4, 1989

[54] GUIDING CATHETER

[75] Inventors: Richard Jaraczewski, Livermore; Mark E. Plaia, Santa Cruz, both of Calif.

[73] Assignee: Devices for Vascular Intervention, Inc., Redwood City, Calif.

[21] Appl. No.: 72,439

[22] Filed: Jul. 13, 1987

[51] Int. Cl.$^4$ .............................................. A61M 25/00
[52] U.S. Cl. .................................... 128/658; 604/282; 138/127; 87/6; 87/8
[58] Field of Search ........................ 604/156, 280, 282; 128/348, 658; 87/1, 6, 8; 138/123, 127

[56] References Cited

U.S. PATENT DOCUMENTS

| | | | |
|---|---|---|---|
| 1,984,475 | 12/1934 | Goodall | 137/96 |
| 2,472,484 | 6/1949 | Krippendorf | 604/282 X |
| 2,962,050 | 10/1957 | Ramberg et al. | 138/60 |
| 3,416,531 | 12/1968 | Edwards | 604/282 X |
| 3,485,234 | 4/1966 | Stevens | 128/2 |
| 3,924,632 | 12/1975 | Cook | 128/348 |
| 4,200,126 | 4/1980 | Fish | 138/127 X |
| 4,425,919 | 1/1984 | Alston, Jr. et al. | 128/658 |
| 4,586,923 | 5/1986 | Gould et al. | 604/95 |

OTHER PUBLICATIONS

Cook, Inc. Radiology, Cardiology, & Surgery Catalog, (1982-84).

Primary Examiner—Stephen C. Pellegrino
Attorney, Agent, or Firm—Townsend and Townsend

[57] ABSTRACT

A torque transmitting guiding catheter adapted for insertion into vascular vessels with a body and a method for its construction is disclosed. The guiding catheter includes a flexible tubular member surrounded by a pair of torque transmitting layers that are formed of a flat braided material. A flexible (plastic) casing that initially is applied as a viscous material impregnates and encases the torque transmitting layer to hold them in place and eliminate their rough edges. The ends of the torque transmitting layers are soldered using a radiopaque solder to enhance the catheter's visibility within a body. The tubular member is also folded about the distal end of the catheter over the distal extremity of at least one of the torque transmitting layers to provide a smooth and soft distal catheter tip. The formed catheter has a flexible curving distal tip. The tip's shape memory is enhanced by at least partially curing the casing material while the tip takes the form of its desired final shape.

32 Claims, 3 Drawing Sheets

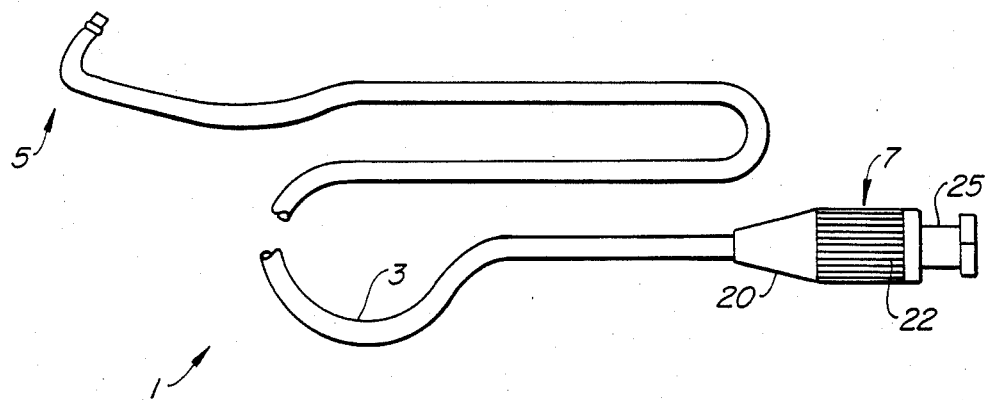
FIG._1.
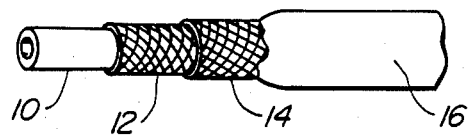
FIG._2.
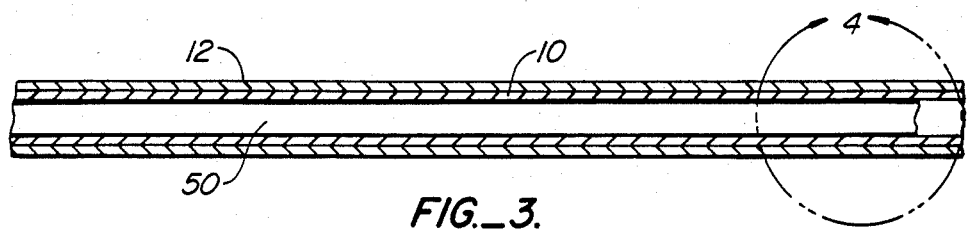
FIG._3.

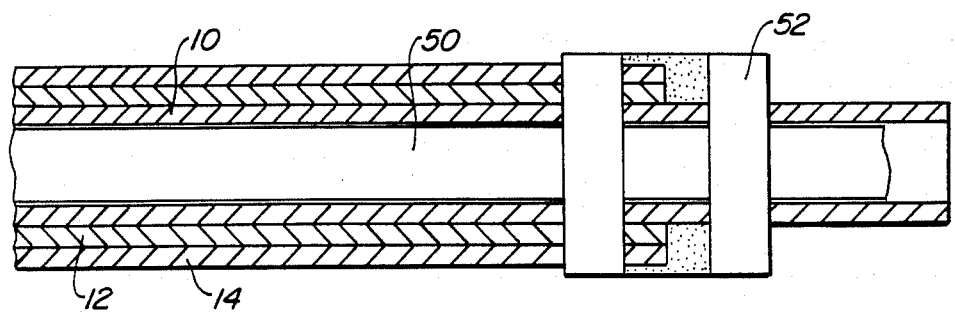
FIG._4.
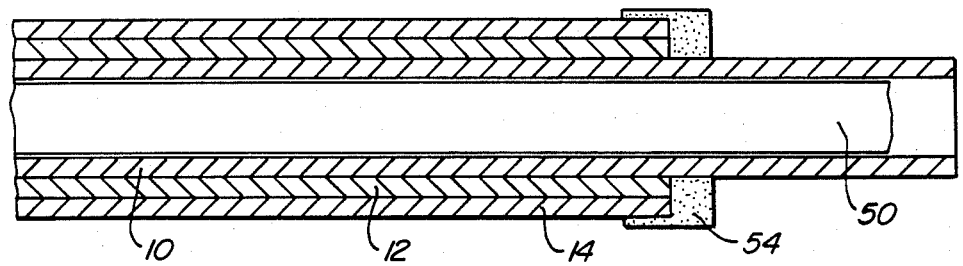
FIG._5.
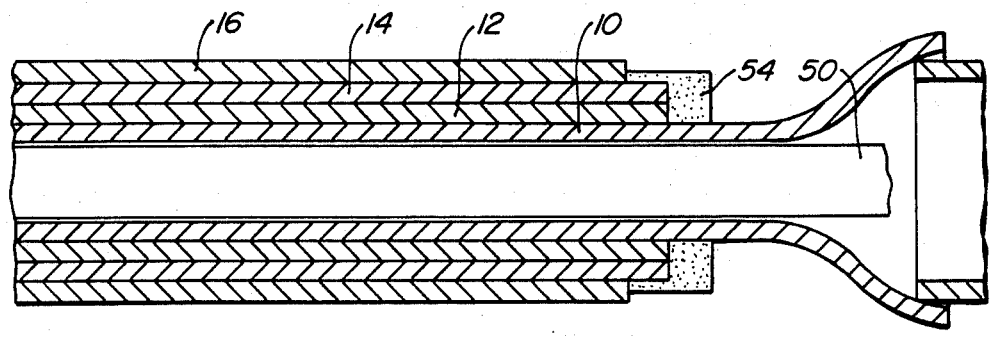
FIG._6.

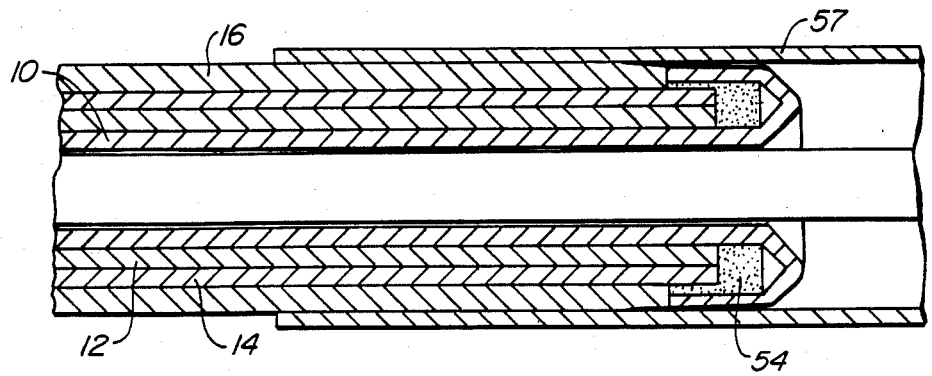
FIG._7.
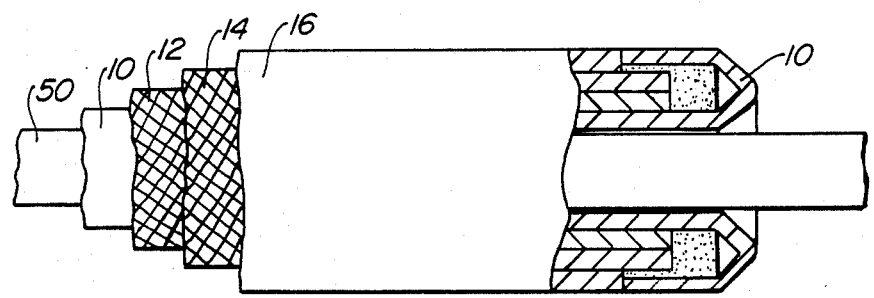
FIG._8.
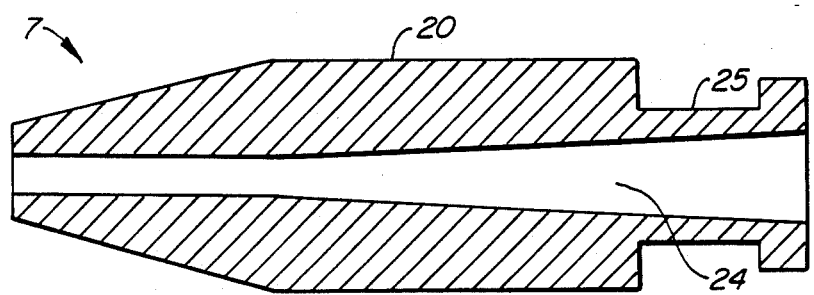
FIG._9.

GUIDING CATHETER

BACKGROUND OF THE INVENTION

The present invention relates generally to guiding catheters adapted for insertion into vascular vessels. More particularly, the present invention relates to an improved catheter construction and fabrication method.

Within the medical community, it is well known that a guiding catheter is a tube having a high degree of directional control that is used to place other catheters having little or no directional control into specific areas of the body. In the field of vascular intervention, guiding catheters are particularly useful to guide angioplasty and atherectomy devices deeply into the body cavity such as, inter alia, in the coronary, cerebral and renal areas. Typically each catheter will have a specific tip shape adapted and sized to facilitate insertion into the intended area of use.

The requirements of a good guiding catheter include high torque transmission for engagement, high inner lumen lubricity to facilitate insertion of secondary devices, low kinking characteristics and good tip memory. Additionally it is desirable to provide a smooth distal leading surface to prevent damage to the vascular vessels. It is also desirable to provide a marker near the distal tip of the catheter to enhance its visibility by a fluoroscope.

A wide variety of prior art devices have been developed that address these design requirements. For example, in U.S. Pat. No. 4,425,919, Alston et al. disclose a torque transmitting catheter that includes a longitudinally pre-oriented thin-walled tubular substrate surrounded by a flat wire braid wound over the substrate and held in place by a thin-walled tubular superstate. While the torque transmitting characteristics of such a device are good, I have discovered that the torque transmission, kink resistance and tip memory features of a guiding catheter can be enhanced by splitting the braided layer into two layers and forming the outer member from a material that forms a composite with the braid layers and the inner substrate.

Similarly, U.S. Pat. Nos. 3,485,234 and 4,586,923 issued to Stevens and Gould et al. respectively, describe the construction of curving tip catheters. The walls of the described tubular bodies include an inner tubular member surrounded by a sheath of braided wire. It appears as though the wire sheath is surrounded by a second tubular member. A separate flexible tip portion that does not include a braided layer is provided to facilitate insertion through a branching network of blood vessels. Like the Alston et al. catheter only a single braided layer is disclosed. Further, the second tubular member is not applied as a viscous material that is cured in the final desired shape of the catheter. Rather, it is applied as an extruded tube.

U.S. Pat. No. 3,924,632 issued to Cook also discloses a catheter body for intubation of body organs and vessels. Like the Stevens and Gould et al. devices, Cook discloses a catheter of construction including two tubular members which enclose a braided structure. In this case, the braids are formed of fiberglass bands.

U.S. Pat. No. 2,962,050 issued to Rambero et al. discloses a flexible wire-reinforced hose that includes a pair of braided wire layers. However, the hose disclosed by Rambero et al. is not encased by the flexible housing that both surrounds and impregnates the braided layers for additional strength. Additionally, no attempt is made to form the hose into a curving tip catheter.

The prior art devices have worked adequately for guiding catheters presently being used for angioplasty and the like. However, they typically have an outer diameter no larger than 9 French. This limits their inner diameter to the range of approximately 5.5 French, which works fine for most angioplasty operations. However, as atherectomy methods, such as those disclosed in co-pending U.S. patent application Ser. Nos. 732,691 filed May 10, 1985 and 045,916 filed May 1, 1987 become more popular, larger diameter guiding catheters become desirable and necessary.

In order to facilitate introduction of the guiding catheter into its intended position, it is desirable to provide a tip that can readily be detected by a fluoroscope to allow the doctor to monitor the catheters progress within the vascular system. Typically a gold or platinum band is placed about the distal tip of the catheter to enhance the guiding catheter's visibility within the body. However, such tips are both expensive and relatively difficult to manufacture.

SUMMARY OF THE INVENTION

Therefore, it is a primary objective of the present invention to provide an improved guiding catheter that is particularly well suited for insertion into specific regions of the vascular system.

A more specific objective is to provide a guiding catheter having particularly high torque transmissivity, low kinking characteristics, and good tip memory.

Another object of the present invention is to provide a guiding catheter that is readily detected by a fluoroscope.

Another object of the invention is to provide a guiding catheter having a smooth and nonabrasive distal end.

Another object of the invention is to provide a guiding catheter having a low friction inner surface to facilitate introduction of other catheters.

Another specific objective of the invention is to provide a guiding catheter construction that will facilitate the fabrication of guiding catheters that have inner diameters that are at least 6 French and outer diameters of 12 French or more.

To achieve the foregoing and other objects and in accordance with the purpose of the present invention, a guide tube is formed that includes a tubular member that has a slick inner surface as a substrate. A first torque transmitting layer is wrapped tightly about the tubular member. A second torque transmitting layer is then wrapped about the first. Preferably, both the first and the second torque transmitting layers are formed of flat braided materials. A flexible plastic casing is then applied as a viscous material and hardened to encase and impregnate both torque transmitting layers.

An annular solder ring is placed near the distal end of the guiding catheter to seal the distal extremity of at least the distal most extending torque transmitting layer. The solder ring is preferably formed of a material that is radiopaque to a fluoroscope to provide a marker that enhances the catheters visibility within a body. Preferably the annular ring is formed of silver solder. The distal end of the tubular member extends beyond the distal extremity of the torque transmitting layers and is folded back over the outer perimeter of the torque transmitting layer to provide a smooth distal tip for the guiding catheter. The smooth tip facilitates insertion into a vascular vessel.

Preferably, the flexible casing is formed of urethanes formed using methylene bis (4-cyclohexylisocyanate) also known as HMDI, as the resin and 4,4' methylene dianiline (also known as MDA) as a hardener.

In a method aspect of the invention, the guide tube portion of the guiding catheter is formed by placing an elongated tubular member on an extended mandril. At least two torque transmitting layers are applied about the tubular member. The first braided layer is applied about the tubular member, while the second braided layer is applied about the first. In one preferred aspect of the method, a mask is placed about the distal extremity of at least one of the braided layers such that the distal extremity of the braided layer is exposed. A thin solder layer is then applied to seal the exposed braided end. In another preferred aspect of the invention, the distal portion of the tubular member is folded back over the distal end of the composite braided tubing such that it covers at least the distal extremity of the distal most extending braided layer. The folded portion of the tubular member is then adhered into place.

The composite braided tubing is coated with a viscous (plastic) casing material such as epoxy or urethane to seal the braided layers to prevent the rough edges of the braided layers from abrading the artery walls when the catheter is in use. The viscous coating material is hardened by placing the composite guide tube into a heated oven to cure. The composite tubing is placed on a forming mandril which replicates the desired shape of the guiding catheter during at least a portion of the curing step. Curing the catheter in its desired final shape enhances the catheter's tip shape memory.

In a preferred aspect of the method, the composite tubing is partially cured after the viscous coating material is applied. The guide tube is then ground to its desired outer diameter and placed on the forming mandril to complete the curing step.

In an alternative aspect of the method, the tip region of the guiding catheter is coated with a softer coating material than is used on the catheter shank in order to provide a more flexible tip. Similarly, several different levels of flexibility may be developed along the guide tube by varying the thickness and hardness of various specific coats of casing materials applied to form the flexible casing.

BRIEF DESCRIPTION OF THE DRAWING

The features of the present invention that are believed to be novel are set forth with particularity in the appended claims. The invention, together with further objects and advantages thereof, may best be understood by reference to the following description taken in conjunction with the accompanying drawings in which:

FIG. 1 is a side elevational view of a guiding catheter formed in accordance with the present invention.

FIG. 2 is a cut-away side view displaying the construction of the guide tube portion of the catheter shown in FIG. 1.

FIG. 3 is a cut-away side elevational view of a tubular member that is mounted on a mandril in preparation for forming a guiding catheter in accordance with the present invention.

FIG. 4 is a cut-away side elevational view highlighting the area within circle 4 of FIG. 4 and showing a guiding catheter under construction and undergoing the soldering step.

FIG. 5 is a cut-away side elevational view of the region shown in FIG. 4 after a soldering step in accordance with the present invention has been completed.

FIG. 6 is a cut-away side elevational view of the region shown in FIGS. 4 and 5 with the folding sleeve in position to fold the expanded portion of the tubular member back over the distal extremity of the torque transmitting sections in accordance with an embodiment of the present invention.

FIG. 7 shows a cut-away side elevational view of the embodiment shown in FIG. 6 with the folding sleeve fully extended.

FIG. 8 is a partially cut-away side elevational view of the distal extremity of the guiding catheter shown in FIG. 1.

FIG. 9 shows an embodiment of a torque transmitting handle suitable for use with the present invention.

DETAILED DESCRIPTION OF A PREFERRED EMBODIMENT

As illustrated in the drawings, with particular reference to FIG. 1, an embodiment of the guiding catheter 1 of the present invention includes an extended guide tube portion 3 having a shaped distal tip 5 and an attachment mechanism 7 on its proximal end.

Referring particularly to FIGS. 2 and 3, the guide tube 3 is comprised of multiple layers including an interior flexible tubular member 10 that is overlaid by two torque transmitting layers 12 and 14. Torque transmitting layers 12 and 14 are separately formed of braided materials with torque transmitting layer 12 tightly overlaying tubular member 10 and torque transmitting layer 14 overlaying the first. The outer torque transmitting layer 14 is encased and impregnated by a flexible casing 16 which is applied as a viscous material and cured to harden as opposed to applying an outer tubular member. It will be appreciated that additional torque transmitting layers formed of either braided or nonbraided materials could be used to accommodate the design requirements of a particular application.

It is essential that the materials used to form all components of the guiding catheter be biocompatible with blood. This is particularly important for the flexible tubular member 10 and the flexible casing 16 which will generally directly contact the bloodstream during use. Tubular member 10 is formed of a flexible material having a slick interior surface in order to provide a high inner lumen lubricity. It is important to provide a low friction inner surface to facilitate the introduction of other catheters such as angioplasty and atherectomy devices. By way of example, a suitable material for forming tubular member 10 is polytetrafluoroethylene.

Torque transmitting layers 12 and 14 are formed of a flat braided material. A braided construction is particularly well suited for the torque transmitting layers since they are quite flexible yet they have good torque transmitting capabilities. Flat braids are particularly useful since they have significantly larger torque carrying capacities than correspondingly sized round braids and they are less prone to kinking. The flexibility torque transmitting characteristics of the braided material may be further altered by varying the density of the braids (i.e the number of braid pics per inch).

I have also discovered that it is advantageous to incorporate at least two braided layers into the catheter design as opposed to utilizing a single thicker layer. The duel layer structure is advantageous due to its improved torque transmitting verses flexibility characteristics. This is particularly important for larger diameter catheter since the outer catheter dimensions are limited by the size of the vascular vessels through which they are expected to pass. Thus, in order to maximize the catheter's inner diameter the thickness of the catheter walls must be kept to a minimum.

The braided torque transmitting layers 12 and 14 may be formed of any braided material having high torque transmitting verses flexibility characteristics. By way of example, appropriate braided materials include stainless steel and Kevlar TM flat ribbons. Particularly suitable ribbon sizes have cross-sectional dimensions in the range of 0.0005" by 0.001" to 0.003" by 0.006". It will be appreciated that dissimilar materials may be used to form a single torque transmitting layer. Thus, by way of example, a braid may incorporate one or more gold or silver strands together with the stainless steel or Kevlar TM strands, in order to increase the radio opacity of the guiding catheter's shaft. Alternatively, Kevlar TM and stainless steel ribbons can be braided together to increase flexibility.

The flexible casing 16 is applied as a viscous material which allows it to both coat and impregnate the braided torque transmitting layers 12 and 14. After the coat has been applied, it is subsequently hardened, thus integrally bonding the torque transmitting layers to the casing 16. The integral bond between the casing 16 and the outer torque transmitting layers 12 and 14 substantially increases the torque transmitting capabilities of the guiding catheter 1, when compared to alternative mechanisms for placing a flexible shroud about the catheter, such as may be accomplished by heat shrinking a tubular member.

There are numerous materials that could be used to form flexible casing 16 including numerous epoxies and polyurethanes. However, I have discovered that urethanes formed using methylene bis (4-Cyclohexylisocyanate) also known as HMDI as the resin with 4,4'-Methylene Dianiline (also known as MDA) as the hardener, available from CONAP, Inc. of Olean, N.Y. are particularly well suited for forming the casing. Various polyols may be added to the HMDI/MDA mixture to vary the hardness of the final urethane. Alternatively, other conventional hardeners such as amines may be used to achieve the same or similar properties. The unexpected suitability of this group of urethane compounds stems primarily from their particularly good torque transmitting capabilities for a given flexibility.

As will be appreciated by those skilled in the art, the flexibility and the torque transmitting capabilities of a guiding catheter so constructed will be a function of several factors. The primary factors include, the material used to form the flat braided torque transmitting layer, its braid density (i.e. the number of pics per inch), the material used to form the casing and the respective thicknesses of both the torque transmitting layers as well as the casing. To a certain degree, flexibility comes at the expense of torque transmitting ability. However, the primary advantage of the construction of the present invention is that it provides a structure that maximizes the torque transmitting capabilities for given materials that comprise the catheter walls.

Depending upon the region of the body into which the catheter is intended to be inserted, various degrees of flexibility will be required. It is frequently desirable to provide different levels of flexibility to the shaft, arch and tip regions in order to accommodate insertion into specific regions of the body. Specifically, the tip normally must be quite flexible in order to pass through particularly tortuous portions of the vessel while the shaft, which typically passes only through larger and straighter portions of the vessel, must be capable of transmitting larger torques. This varied flexibility may be accomplished through a wide variety of mechanisms including, inter alia, using urethanes having different durometers in the various regions, eliminating the tip portion of the second braided layer or adding additional braided torque transmitting layers to the shaft portion, and altering the braid densities of the torque transmitting layers along the catheter's length.

It will be appreciated by those skilled in the art that the guide tube portion of guiding catheter 1 has a relatively smooth and slick surface. Therefore, it is difficult for the doctor to get a satisfactory grip on the guide tube itself in order to effect rotation deep within the body cavity. To overcome this limitation, attachment mechanism 7 is provided near the proximal end of guide tube 3. As can be seen in FIGS. 1 and 10, the attachment mechanism 7 includes a torque handle 20 and a standard medical female luer connector 25. Torque handle 20 is provided to enhance the doctors ability to rotate the catheter within the body. As is emphasized by FIG. 10, torque handle 20 has a knurled outer surface 22 to further enhance the doctors grip. Preferably, the torque handle 20 will have an outer diameter in the range of 0.25" to 1.00", such a large diameter helps facilitate the finger torquing method of guide placement.

The attachment mechanism 7 also includes a central borehole 24 which is adapted to tightly receive guide tube 3. The bond between guide tube 3 and attachment mechanism 7 may be made by an adhesive such as epoxy or by any other conventional fastening means. The female luer 25 provided on the distal extremity of guide tube 3 facilitates connection with standard medical instruments. The luer 25 may be formed of plastic integrally with torque handle 20 as in the embodiment shown in the drawings, or the two components may be formed separately.

It will be appreciated that the attachment mechanism 7 could be formed to take the shape of any conventional attachment for the proximal ends of guiding catheters. For example, the attachment mechanism 7 could take the form of a conventional Y-shaped hemostasis valve having duel female luers. In such an arrangement, one of the female luers would lead through an open channel in the attachment mechanism directly to the lumen formed within the guide tube 3 while the other luer would be blocked by a hemostatis seal.

Referring next to FIGS. 3-8, the fabrication of a guiding catheter in accordance with a method aspect of the present invention will be described. An elongated Teflon TM tube 10 is first cut to a length that is slightly longer than the desired length of the guiding catheter 1. The tubular member 10 is then placed over a mandril 50 which preferably has an outer Teflon TM coat. An ordinary braiding machine such as Model #2, manufactured by The New England Butt Co., is then used to lay the first torque transmitting layer 12 about the tubular member 10. The density of the braid is adjusted to a predetermined level to provide a particular flexibility as previously discussed. By way of example, a suitable braid density would be in the range of 20-100 pics per inch with each torque transmitting layer being formed of in the range of 8 to 64 ribbon strands. A preferred number of ribbon strands is approximately 16.

After the first torque transmitting layer 12 has been applied, the second torque transmitting layer 14 is layed thereover. It should be appreciated that additional braided torque transmitting layers could be laid thereover and that not all such layers need be formed of the same material or by ribbons of the same size or shape. The braid density and constituents of the second and further torque transmitting layers may be adjusted to suit the particular requirements of the guiding catheter being fabricated.

After each of the braided layers has been applied, masks 52 are placed over both the distal and proximal ends of the braided torque transmitting layers 12 and 14. The braid ends are then soldered to prevent them from unraveling and to eliminate their roughened ends. Mask 52 is provided only to control the size of annular solder ring 54. Preferably a solder that is radiopaque to X-rays is used to seal at least the distal ends of the braided torque transmitting layers 12 and 14, thereby enhancing the catheters visibility on a fluoroscope. Suitable radiopaque solders would include silver solder and other solders containing radiopaque materials. By way of example, suitable radiopaque materials would include gold, platinum, and tantelum. It will be appreciated that the braided layers may be soldered either independently immediately after being laid or jointly when their ends are substantially adjacent.

Also by way of example, the annular rings 54 may be formed by placing thin solder layers about torque transmitting layer 14 at a distance that determines the final catheter length. The solder may be applied by wrapping a 0.015" solder ribbon in a similarly sized gap between a pair of opposing heat shrunk sleeves that are placed about the composite braided structure. A heat gun may then be used to band the solder ring to the braided torque transmitting layers 12 and 14. The excess braid is then trimmed via electro polishing or mechanical cut off.

Referring next to FIGS. 6 and 7, after the annular ring 54 has been applied, folding sleeve 57 is inserted into the extended region of tubular member 10. Both the distal and proximal ends of tubular member 10 are then folded back over their respective opposing ends of the least one of the torque transmitting layers as can be seen in FIGS. 6 and 7. The folding sleeve first engages the interior portion of tubular member 10 and is advanced as seen in FIG. 7 thereby accomplishing the fold. Epoxy is used to adhere the folded portion of the tubular member to the solder and the braided torque transmitting layers.

As can be seen by referring to FIG. 6, a viscous casing material such as polyurethane is applied about the outer torque transmitting layer 14. It may be desirable to apply multiple coats of the casing material in order to adequately cover the braided surface and to attain the desired catheter thickness. In the embodiment described herein, a urethane formed of methylene bis (4-Cyclohexylisocyanate) and 4,4'-methylene dianiline is used as the casing material. It will be appreciated by those skilled in the art that there are several alternative polyurethanes and epoxies that may be substituted as the viscous casing material. As previously discussed, it may be desirable to apply polyurethanes having different hardnesses to the distal and proximal ends of guiding catheter 1 in order to attain the necessary flexibility verses strength characteristics for various regions of the guide tube 3. The urethane may be applied in any conventional manner. By way of example it may be applied either by hand on a spin coater or by drawing the composite structure through a coating die.

Multiple coats of the casing material are generally applied. One or two thin coats of a urethane may initially be applied uniformly across the composite braided structure. One or more thicker urethane coats may then be applied about the uniform coats. Since many of the desirable specific catheter shapes require flexible tips, urethanes having different durometers may be used for the tip and shank regions of the catheter. When the guiding catheter is intended to reach places deep within the vascular system through particularly tortuous vessels, it may be desirable to have three or more progressively softer regions of the catheter. To facilitate such a structure, urethanes having different durometers could be applied to the various regions of the guide tube 3. It will be appreciated that softer urethanes will provide more flexibility to the tip regions.

After the polyurethane casing has been applied, the composite guide tube 3 is placed in an oven for a short time and allowed to partially harden. By way of example, the initial curing step may be in the range of 1 to 16 hours at an oven temperature in the range of 60 to 80 degrees Centigrade. The composite catheter is then withdrawn from the oven and ground to the desired thickness. It will be appreciated that the actual curing time and temperatures will vary widely with the particular epoxies and/or urethanes being used. For example, some casing materials may be cured at room temperature.

I have discovered that the tip memory of the catheter may be significantly improved by at least partially curing the flexible casing materials while the guide tube 3 is positioned in substantially the same shape that it will ultimately be used in. Preferably, the catheter is removed from the oven after partial curing, ground to its desired width, and then placed on a tip forming mandril that duplicates the desired shape of the catheter being formed. The catheter is then reinserted into the oven to complete the curing step while disposed on the tip forming mandril. It will be appreciated that the shape of the tip forming mandrils may be varied to duplicate any conventional guiding catheter shape. By way of example, a particularly appropriate cure may take the form of placing guide tube 3 in an oven at approximately 80° Centigrade for about two hours.

The specific presently preferred construction of a 7F by 9F coronary guiding catheter as shown in FIG. 1 will next be described. The tubular member 10 is formed from a 0.093 inch outer diameter etched Teflon TM tube. The tubular member 10 is then placed on a 0.091 inch diameter mandril. The first torque transmitting layer 12 which is formed by braiding stainless steel ribbons having rectangular cross sectional dimensions of 0.0015 inches by 0.005 inches is then applied about the tubular member 10. The braid density is set in the range of 20 to 100 pics per inch. An exemplary braid density is approximately 60 pics per inch. The second torque transmitting layer 14 is then applied about the first using an identical process. Although the second braided layer preferably has a braid density in the same range as described above, it will be appreciated that the braid density of the two layers are completely independent of one another. After the braided torque transmitting layers have been applied, both ends are masked and soldered using a tin silver solder.

After soldering, the exposed braided area behind each annular ring is masked with a water soluble wax. The exposed ends of the braid/mandril assembly is then placed in an electrolyte solution. The braided layers 12 and 14 are then electropolished from the extremity of the braids to the nearest annular ring 54 thereby removing any excess braid and eliminating rough ends. It should be appreciated that the ends could be smoothed by a mechanical polish as well. After polishing, a small piece of heat shrink tubing is placed over the annular rings 54 to protect it from exposure to the urethane flexible casing 16 which is applied in the next step.

Conathane TU-960 polyurethane, manufactured by CONAP of Olean, N.Y. is applied along the entire shaft length. The urethane may be applied to the composite braided structure while it is being rotated about a spin coater either by hand, dip coating, spraying or through the use of an alternative appropriate coating device such as a rubber gasket that tightly receives the braided structure. Dip coating and spraying the urethane are alternative methods of thin coat application as viscosity may be modified using heat or surfactant type additives. Two thin urethane layers are initially applied over the entire length of the catheter. The guide tube 3 is then placed in an oven at a temperature of approximately 65 degrees Centigrade for approximately 30 seconds in order to partially harden the urethane casing. After being removed from the oven, a third layer of the same urethane is thickly coated about all but the distal most half inch of the composite braided structure. To provide a more flexible tip, the distal most half inch of the catheter is thickly coated with a softer urethane such as Conathane TU-900. The composite structure is once again placed in the oven for approximately two hours at 80 degrees centigrade to partially cure.

After the partial curing, the guide tube 3 is removed and a centerless grind reduces its outer diameter to 0.118 inches. The heat shrink tubes protecting the annular rings are removed and the exposed ends of tubular member 10 are folded back over the distal extremity of the torque transmitting layers. The folded ends of tubular member 10 are then epoxied into place. The guide tube 3 is inserted over a forming mandril designed such that the guide tube will take the desired shape of the completed guiding catheter. The forming mandril with the guide tube still in place is then inserted into an oven and heated for approximately 48 hours at approximately 80 degrees Centigrade. The guiding catheter is completed by epoxying attachment mechanism 7 onto the proximal extremity of the guide tube. The completed guiding catheter 1 is then sterilized and packaged in a sterile unit using conventional techniques.

Although only a few embodiment of the present invention have been described in detail, it should be understood that the present invention may be embodied in many other specific forms without departing from the spirit or scope of the invention. Particularly, it should be understood that the specific materials used for the tubular member, the braided torque transmitting layers, and the flexible casing may be varied to a wide degree without departing from the spirit of the invention. Depending upon the specific flexibility and torque transmitting characteristic required by a specific design, it may be desirable to vary the hardness of the casing materials and/or vary the density or the cross-sectional directions of the braids in order to provide the desired flexibility. Similarly, it should be appreciated that the length of the two torque transmitting layers need not be the same, and that their respective lengths may be altered to accommodate any desired flexibility. Further, it may be desirable to incorporate more than two torque transmitting layers, and the braid ribbons used to form the various torque transmitting layers need not be the same size.

Additionally, the specific urethanes or epoxies used and their respective hardnesses may be widely varied to facilitate a desired flexibility. It should be understood that the specific curing times and temperatures mentioned are by way of example and as is well known in the art, the curing times and temperatures may be widely varied without degrading the integrity of the hardened structure. Therefore, the present examples and embodiments are to be considered as illustrative and not restrictive, and the invention is not to be limited to the details given herein, but may be modified within the scope of the appended claims.

I claim:

1. In a guiding catheter having distal and proximal ends and adapted for introduction into a vascular vessel,
   an elongated tubular member having a slick interior surface,
   a first torque transmitting layer tightly overlaying said elongated tubular member and formed of a flat braided material,
   a second torque transmitting layer tightly overlaying said first torque transmitting layer and formed of a flat braided material, and
   a flexible casing that encases and impregnates said first and second torque transmitting layers, said flexible casing being formed from a plurality of coatings having dissimilar durometers,
   whereby said flexible casing is applied to the braided layers as a viscous material and then hardened so that it seals and covers the braided torque transmitting layers.

2. A guiding catheter as recited in claim 1 wherein the distal extremity of said first and second torque transmitting layers occur at different points along the length of the guiding catheter.

3. A guiding catheter as recited in claim 1 wherein the distal extremity of said first and second torque transmitting layers are substantially co-planar.

4. A guiding catheter as recited in claim 1 wherein said braided materials are formed of flat ribbons.

5. A guiding catheter as recited in claim 4 wherein said ribbons have rectangular cross-sectional dimensions in the range of ½ mil by 1 mil to 3 mils by 6 mils.

6. In a guiding catheter having distal and proximal ends and adapted for introduction into a vascular vessel,
   an elongated tubular member having a slick interior surface,
   a first torque transmitting layer tightly overlaying said elongated tubular member and formed of a flat braided material,
   a second torque transmitting layer tightly overlaying said first torque transmitting layer and formed of a flat braided material,
   a flexible casing that encases and impregnates said first and second torque transmitting layers, and
   an annular soldered band formed near the distal tip of the guiding catheter for sealing the distal end of at least one of said torque transmitting layers, whereby said annular solder ring is adapted for enhancing the catheter's visibility within a body.

7. A guiding catheter as recited in claim 6 wherein said annular solder band is formed of a silver solder.

8. In a guiding catheter having distal and proximal ends and adapted for introduction into a vascular vessel,
   an elongated tubular member having a slick interior surface,
   a torque transmitting layer overlaying said elongated tubular member and formed of braided material,
   a flexible casing that encases said torque transmitting layer, and
   wherein the distal end of the elongated tubular member is folded over the distal extremity of said torque transmitting layer to provide a smooth distal tip for the guiding catheter.

9. A guiding catheter as recited in claim 1 wherein said flexible casing is formed of urethanes made by reacting methylene bis (4-Cyclohexylisocyanate) with 4,4' methylene dianiline.

10. A guiding catheter as recited in claim 1 wherein said flexible casing is formed of materials having a hardness in the range of 80 Shore A to 60 Shore D.

11. A guiding catheter as recited in claim 1 wherein said guiding catheter includes a shaft region and a tip region and said plurality of coatings are arranged such that said tip region is more flexible than said shank region.

12. A guiding catheter as recited in claim 1 wherein said first and second torque transmitting layers are formed of braided stainless steel having a density in the range of 20-100 pics per inch.

13. A guiding catheter as recited in claim 1 further comprising side holes within the walls of the guiding catheter for facilitating the flow of blood through the catheter.

14. A guiding catheter as recited in claim 1 further comprising a torque handle having an outside diameter in the range of 0.25 inches to 1.00 inches disposed adjacent the proximal end of said catheter for enhancing a user's ability to rotate the catheter within a vessel.

15. A guiding catheter as recited in claim 1 further comprising a female luer extending from the proximal extremity of the guiding catheter.

16. A guiding catheter as recited in claim 15 further comprising a torque handle disposed adjacent the proximal end of said catheter for enhancing a user's ability to rotate the catheter within a vessel, wherein said torque transmitting handle and said luer are formed as a single piece.

17. In a guiding catheter having distal and proximal ends and adapted for introduction into a vascular vessel,
   an elongated tubular member having a slick interior surface,
   a torque transmitting layer tightly overlaying said elongated tubular member and formed of a braided material, said torque transmitting layer having distal and proximal ends,
   a flexible casing that encases said torque transmitting layer,
   an annular solder band formed of a material that is radiopaque to X-rays and positioned near the distal tip of the guiding catheter for sealing the distal end of said torque transmitting layer.

18. A guiding catheter as recited in claim 17 wherein said annular solder band is formed of a silver solder.

19. A guiding catheter as recited in claim 17 wherein said annular band is formed of a solder including a radiopacity increasing metal from the group of gold, platinum and tantelum.

20. A guiding catheter as recited in claim 17 wherein the distal end of said elongated tubular member is folded back over said annular solder band to provide a smooth distal tip for the guiding catheter.

21. A method of fabricating a guiding catheter having distal and proximal ends and adapted for introduction into a vascular vessel comprising the steps of:
   placing an elongated tubular member on an extended mandril;
   forming a first torque transmitting layer by braiding a plurality of ribbons about the tubular member;
   forming a second torque transmitting layer by braiding a plurality of flat ribbons about the first torque transmitting layer to form a composite braided structure;
   coating the composite braided structure with a viscous material to form a flexible casing;
   folding the distal portion of the tubular member back upon itself to encase the distal extremity of at least the distal most one of said torque transmitting layers; and
   hardening the coating material.

22. A method of fabricating a guiding catheter as recited in claim 21 together with the step of placing a mask about the distal extremity of at least a selected one of the braided torque transmitting layers and soldering within an open area of the mask to form an annular ring that seals the selected braid end.

23. A method of fabricating a guiding catheter as recited in claim 21 together with the step of placing the composite guiding catheter onto a forming mandril for at least a portion of the hardening step, whereby said forming mandril causes the catheter to substantially take its desired final form.

24. A method of fabricating a guiding catheter as recited in claim 23 further comprising the step of grinding the coating material to a desired width after the coating material has partially cured, but before it is completely cured.

25. A method of fabricating a guiding catheter having a nonlinear shape and adapted for introduction into a vascular vessel, the catheter including an inner tubular member, at least one torque transmitting layer formed of a braided material, and a flexible casing formed of at least one flexible coating material, the method comprising the steps of:
   forming said torque transmitting layer by braiding a plurality of braid strands about the tubular member;
   applying at least one layer of a first viscous coating material about the torque transmitting layers such that a viscous material impregnates and encases the torque transmitting layer;
   hardening the viscous coating material;
   causing the guiding catheter to take substantially its ultimately desired shape for at least a portion of the curing step.

26. A method of fabricating a guiding catheter as described in claim 25, further comprising the step of placing at least one layer of a second viscous coating material about a first portion of the braided torque transmitting layer, said second viscous coating material having a different durometer than said first viscous coating material, whereby said first portion of the braided torque transmitting layer has a different flexibility than a second portion of the torque transmitting layer.

27. A method of fabricating a guiding catheter as recited in claim 25, further comprising the step of:

folding the distal portion of the tubular member back upon itself to encase the distal extremity of the torque transmitting layer; and securely adhering the folded portion of the tubular member into place.

28. A method of fabricating a guiding catheter as recited in claim 25, wherein:

said hardening step includes a partial curing step wherein said guide tube is heated to effect a partial cure, and a final curing step; and said forming step is facilitated by placing the guide tube over a forming mandril after the partial curing step.

29. A method of fabricating a guiding catheter as recited in claim 28, further comprising the step of grinding the coating material to a desired width after the partial curing step, but before the guide tube is placed on the forming mandril.

30. In a guiding catheter having distal and proximal ends and adapted for introduction into a vascular vessel, a flexible elongated tubular member having a slick interior surface, a first torque transmitting layer tightly overlaying said elongated tubular member and formed of a flat braided material, a second torque transmitting layer tightly overlayping said first torque transmitting layer and formed of a flat braided material, and a flexible casing that encases and impregnates said first and second torque transmitting layers, whereby said flexible casing is applied to the braided layers as a viscous material and then hardened so that it seals and covers the braided torque transmitting layers while remaining flexible.

31. A guiding catheter as recited in claim 30 wherein said braided materials are formed of flat ribbons.

32. A guiding catheter as recited in claim 31 wherein said ribbons have rectangular cross-sectional dimensions in the range of ½ mil by 1 mil to 3 mils by 6 mils.

* * * * *